United States Patent [19]

Lin

[11] Patent Number: 5,097,065
[45] Date of Patent: Mar. 17, 1992

[54] PROCESS FOR SYNTHESIS OF A NOVEL AMINO ACID FROM STYRENE, ACETAMIDE AND SYNGAS

[75] Inventor: Jiang-Jen Lin, Round Rock, Tex.

[73] Assignee: Texaco Inc., White Plains, N.Y.

[21] Appl. No.: 218,776

[22] Filed: Jul. 14, 1988

Related U.S. Application Data

[63] Continuation-in-part of Ser. No. 720,228, Apr. 5, 1985, abandoned.

[51] Int. Cl.$^5$ .............................. C07C 229/36
[52] U.S. Cl. ...................................... 562/450
[58] Field of Search ............... 560/41; 562/450

[56] References Cited

U.S. PATENT DOCUMENTS 3,766,266  10/1973  Wakamatsu et al. ............... 562/450
4,675,439   6/1987  Mita et al. ............................ 562/450

OTHER PUBLICATIONS

Tou et al., J. Org. Chem., vol. 49, pp. 1135-1136 (1984).
Falbe, "Carbon Monoxide in Organic Synthesis", pp. 3-45 (1970).

*Primary Examiner*—James H. Reamer
*Attorney, Agent, or Firm*—Jack H. Park; Kenneth R. Priem; Cynthia L. Kendrick

[57] ABSTRACT

A phenyl substituted amino acid derivative is synthesized by reacting styrene, acetamide and synthesis gas with a bimetallic catalyst comprising a rhodium-containing compound and a cobalt-containing compound, optionally in the presence of a solvent at a pressure of at least 500 psi and a temperature of at least 50° C. The novel amino acid contains a carboxylic acid group, an acetamido group at the alpha-position and a phenyl group at the beta-position.

1 Claim, No Drawings

PROCESS FOR SYNTHESIS OF A NOVEL AMINO ACID FROM STYRENE, ACETAMIDE AND SYNGAS

CROSS REFERENCE

This is a continuation-in-part of application Ser. No. 06/720,228 filed April 5, 1985 now abandoned.

FIELD OF THE INVENTION

This invention relates to the synthesis of a novel type of N-acetylamino amino acid, Beta-phenyl-N-acetyl-amino acid.

More particularly this invention uses a bimetallic rhodium-cobalt catalyst to synthesize a novel phenyl substituted amino acid from styrene, acetamide and synthesis gas using low pressures and temperatures.

BACKGROUND OF THE INVENTION

Early attempts were unsuccessfully made to synthesize α-amino acids or derivatives thereof by reacting a Schiff base or a nitrile with carbon monoxide and hydrogen. [Bull. Chem. Soc. Japan 33 (160) 78]

U.S. Pat. No. 3,766,266 to Wakamatsu discloses a method of producing an N-acyl-α-amino acid which comprises holding an aldehyde, an amide of a carboxylic acid and carbon monoxide at a temperature of 10° to 300° C. and a pressure of at least 500 atm. in the presence of a carbonylation catalyst until said N-acyl-α-amino acid is formed.

In *Chem. Comm.* 1540 (1971), Wakamatsu, et al. first disclose a cobalt-catalysed reaction which gives various N-acyl amino-acids from an aldehyde, an amide and carbon monoxide. In this disclosure, while benzaldehyde was used as the starting aldehyde, there was no corresponding α-phenyl-substituted amino acid obtained. Instead of the expected amino acid product, a imine was obtained by a simple "amination" reaction.

An article by Parnaud, et al., in *Journal of Molecular Catalysis*, 6 (1979) 341-350, discusses the synthesis potential and the catalytic mechanism for the reaction wherein N-acyl-α-amino acids are produced by reacting an aldehyde, CO and an amide in the presence of dicobalt octacarbonyl.

In amidocarbonylation, the aldehyde can be generated in situ from allyl alcohol, oxiranes, alcohols and olefins followed by the reaction with an amide and carbon monoxide to produce an N-acyl-α-amino acid.

A related Patent, U.S. Pat. No. 3,996,288 discloses that when an alcohol or certain of its ester derivatives is held at 50° C. to 200° C. and 10 to 500 atm. in the presence of hydrogen, carbon monoxide, the amide of a carboxylic acid and a carbonylation catalyst, an aldehyde having one more carbon atom than the alcohol or ester is formed in good yield. If the amide has at least one active hydrogen atom on its amide nitrogen, it further reacts with the aldehyde and carbon monoxide to form an N-acylamino acid.

Hirai, et al. discuss a process for combining the transition metal catalyzed isomerization of allyl alcohol to aldehyde and cobalt catalyzed amidocarbonylation to provide a route from allylic alcohols to N-acyl-α-amino acids. See *Tetrahedron Letters*, Vol. 23, No. 24, pp. 2491-2494, 1982.

U.S. Pat. No. 4,264,515 discloses a process for obtaining terminal N-acyl-α-amino acids by a reaction catalyzed by a cobalt carbonylation catalyst wherein the aldehyde is produced in situ from olefins and CO/H$_2$ mixtures. An unsaturated vegetable oil or C$_8$-C$_{30}$ mono olefinic compound is reacted with an amide, carbon monoxide and hydrogen in the presence of a cobalt catalyst. The process is operated in one step and provides for increased selectivity.

None of these references suggests or discloses the one step synthesis of a novel phenyl substituted amino acid, Beta-phenyl-N-acetyl-alpha-amino acid, in yields as high as 75%. The product can be hydrolyzed into beta-phenyl substituted amino acid. The phenyl substituted amino acid derivative can be converted to other products via sulfonation. These products are useful as chelating agents. They are also useful pharmacological chemicals, e.g. U.S. Pat. No. 4,551,279.

SUMMARY OF THE INVENTION

This invention concerns a method for synthesizing a novel phenyl substituted amino acid, exemplified by Beta-phenyl-N-acetyl-alpha-amino acid which comprises contacting a mixture of styrene, acetamide and syngas (carbon monoxide and hydrogen) with a catalyst comprising a bimetallic rhodium-cobalt catalyst optionally in the presence of a solvent at a pressure of at least 500 psi and a temperature of at least 50° C.

The novel product contains an N-acetylamino acid group with a phenyl-substituent at the beta-position.

DETAILED DESCRIPTION OF THE INVENTION

In the narrower and more preferred practice of this invention phenyl substituted amino acids are prepared from a mixture of styrene, acetamide, carbon monoxide and hydrogen by a process which comprises contacting said mixture with a catalyst system comprising a rhodium-cobalt catalyst in a substantially inert solvent at a temperature of at least 50° C. and a pressure of at least 500 psi until substantial formation of the desired amino acid has been achieved.

The reaction can best be represented by the following Equation 1:

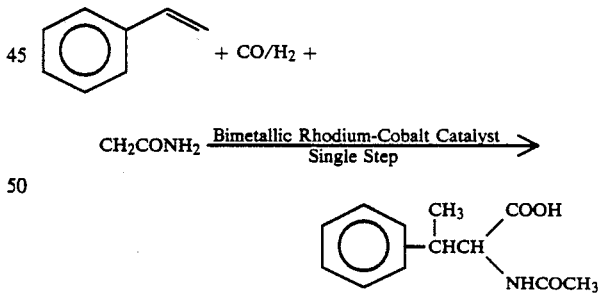

Recovery of the Beta-phenyl-N-acetyl-alpha-amino acid from the reaction product can be carried out in any convenient or conventional manner such as by distillation, extraction, filtration, crystallization, etc. In the embodiment of this invention the product was recovered by a simple extraction procedure. The product was identified by HMR.

The catalyst system suitable for the practice of this invention comprises a bimetallic rhodium-cobalt catalyst optionally in a substantially inert solvent.

In the catalyst system of this invention the rhodium-containing compound and cobalt-containing compound are believed to be in complex equilibrium during amidocarbonylation in such a way that this catalyst system provides two important advantages over the use of cobalt alone:

1) It gives higher yields and selectivities of the novel amino acid product than ca be obtained with a catalyst which utilizes solely a cobalt-containing compound dispersed in a solvent.
2) It is possible to employ low-pressure operating conditions, such as a pressure of less than 1000 psi and a 100° C. reaction temperature.

The rhodium-containing compound may take many different forms. For instance the rhodium could be added in the form of an oxide, a salt of a mineral acid, the salt of a suitable organic carboxylic acid or a carbonyl, hydrocarbonyl or derivative thereof.

In the process of this invention it is preferable that the rhodium compound contain a triphenylphosphine ligand. Compounds which work well in this respect include those where the rhodium is added to the reaction zone as a carbonyl, hydrocarbonyl or substituted carbonyl species wherein the substituted group is triphenylphosphine. The preferred compound is hydridorhodium tris(triphenylphosphine)carbonyl, $HRh(CO)(PPh_3)_3$.

The cobalt-containing compound may take many different forms. For instance, the cobalt may be added to the reaction mixture in the form of a variety of inorganic or organic cobalt salts, or cobalt carbonyls. The cobalt may, for example, be added as a cobalt halide such as cobalt bromide or cobalt chloride, or it may be added as the salt of an aliphatic or aromatic carboxylic acid such as, for example, cobalt formate, cobalt acetate, cobalt butyrate, cobalt naphthenate, and cobalt stearate. The cobalt carbonyl may be tetracobalt dodecacarbonyl or dicobalt octacarbonyl. The preferred cobalt-containing compound is dicobalt octacarbonyl.

The physical parameters which are desirable in the feedstock of this invention for producing N-acetylamino acid are:

The starting olefin substrates can be substituted styrene, described by the following structure:

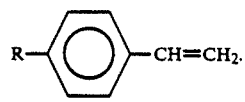

The R-group can be any alkyl, such as methyl, ethyl, hexyl or octyl, at any position, including ortho-, meta- or para-position. The preferred compound is styrene.

Suitable amide-containing coreactants that are useful in the amidocarbonylation reaction have the general structure:

where the $R_1$ and $R_2$ groups may be a combination of aryl, alkyl, arylalkyl and alkylaryl hydrocarbonyl radicals, or hydrogen, including the methyl, ethyl, butyl, n-octyl, phenyl, benzyl, chlorophenyl groupings etc. Examples of suitable amide coreactants include acetamide, benzamide, formamide, n-methylformamide, lauramide and n-methylbenzamide. The preferred coreactant is acetamide.

The carbon monoxide employed need not satisfy particular purity requirements although catalyst contaminants should be avoided if the reaction is intended to continue over an extended period. Particularly in continuous operations, but also in batch experiments, the carbon monoxide and hydrogen gas may also be used in conjunction with up to 10% by volume of one or more other gases. These other gases may include one or more inert gases such as argon, nitrogen and the like or they may include gases that may, or may not, undergo reaction under carbon monoxide hydrogenation conditions, such as carbon dioxide, hydrocarbons, such as methane, ethane, propane and the like, ethers, such as dimethyl ether, methyl ethyl ether and diethyl ether, alkanols, such as methanol, and the like.

As characterized above, this process is operated as a homogeneous liquid phase mixture. The reaction is preferably operated in an inert solvent. Preferred inert solvents are those which permit at least partial dissolution of the cobalt catalyst precursor, the amide and the aldehyde compound. These are generally polar solvents, of the ester, ether, ketone, amide, sulfoxide or aromatic hydrocarbon type, for example.

Methyl and ethyl acetate are examples of suitable solvents. Other polar solvents are ethers, such as p-dioxane, methyl tertiary butyl ether, methyl tertiary amyl ether or tetrahydrofuran, tertiary amides, such as dimethyl formamide, dimethyl sulfoxide and ethylene carbonate.

The preferred solvent is ethyl acetate.

The novel amino acid is often insoluble in the solvent phase. This permits separation of the rhodium catalyst which may dissolve into the solvent phase, with or without prior acidification.

In all these synthesis in order to achieve a high degree of selectivity the amount of carbon monoxide, aldehyde and amide present in the reaction mixture should be sufficient to at least satisfy the stoichiometry of the desired formation of Beta-phenyl-N-acetyl-alpha-amino acid as shown in Equation I above. Excess carbon monoxide over the stoichiometric amount may be present and is desirable.

The quantity of rhodium-containing compound and cobalt-containing compound to be used in the bimetallic catalyst of the invention may vary. The process is conducted in the presence of a catalytically effective quantity of the active rhodium-containing compound and the active cobalt-containing compound which gives the desired product in reasonable yield. The reaction proceeds when employing as little as about 0.01 weight percent, and even lesser amounts of the rhodium-containing compound, along with as little as about 0.1 weight percent of the cobalt-containing compound based on the total weight of the reaction mixture. The upper concentration is dictated by a variety of factors including catalyst cost, partial pressures of carbon monoxide and hydrogen, operating temperature, etc. A rhodium-containing compound concentration of from about 0.01 to about 1.0 weight percent in conjunction with a cobalt-containing compound concentration of from about 0.1 to about 10 percent, based on the total weight of the reaction mixture is generally desirable in the practice of this invention.

Particularly superior results are obtained when the above-noted components of the catalyst system are combined as follows on a molar basis: Rhodium-containing compound to cobalt-containing compound, 1.0:1.0 to 1.0:1000.

The operating conditions may vary over a wide range. The reaction temperature may vary from 25° C. to 300° C. The preferred temperature is from 80° C. to 150° C. The pressure may range from 500 psi to 4000 psi or more. It appears that higher selectivities are obtained when operating at moderate pressures, in the range from 1000 to 3500 psi.

The amidocarbonylation reaction of this invention is best conducted in a carbon monoxide-rich atmosphere, although some hydrogen gas should also be present in order to achieve maximum cobalt catalyst activity. The hydrogen to carbon monoxide molar ratio in the reactor may be varied, for example, within the range from 20:1 to 1:20, but preferably it should be rich in carbon monoxide and the $H_2$:CO ratio should be in the range 5:1 to 1:5.

The desired products of this synthesis are phenyl substituted amino acids. The main desired product, Beta-phenyl-N-acetyl-alpha-amino acid will be formed in significant quantities. Also formed are significant amounts of aldehyde products. Each of these products, including byproducts can be recovered from the reaction mixture by conventional means, e.g. crystallization or filtration.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired amino acid product, and said material may be recovered by methods known to the art, such as filtration, recrystallization distillation, extraction and the like. A fraction rich in the catalyst components may then be recycled to the reaction zone, if desired, and additional products generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analysis, or a combination of these techniques. Analysis have for the most part, been by molar weight; all temperatures are in degrees centigrade and all pressures in pounds per square inch (psi).

The yield of N-acetyl-alpha-amino acid in each synthesis (mole %) is estimated basis equation using the formula:

$$\frac{\text{Moles of Beta-phenyl-N-acetyl-alpha-amino acid obtained}}{\text{Moles of styrene charged}} \times 100\%$$

Generally the reaction can be represented by the following equation:

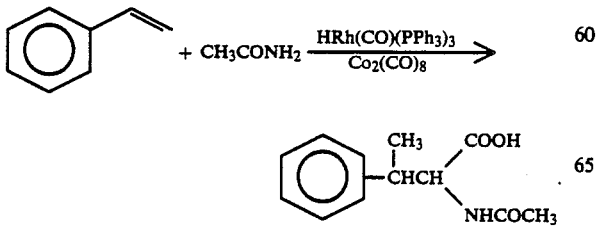

To illustrate the process of the invention, the following examples are given. It is to be understood, however, that the examples are given in the way of illustration and are not to be regarded as limiting the invention in any way.

EXAMPLE I

A glass-lined reactor was charged with HRh(CO)(PPh$_3$)$_3$ (0.092 g, 0.10 mmole), dicobalt octacarbonyl (0.34 g, 1.0 mmole), styrene (5.2 g, 0.05 mole), acetamide (3.0 g, 0.05 mmole) and p-dioxane (10 g). The reactor was purged of air with CO/H$_2$ mixture, then pressured to 500 psi with CO/H$_2$ (1:2 molar ratio). The system was heated to 100° C. and the pressure was raised to 2000 psi with CO/H$_2$ mixture (1:2). After 4 hours reaction time, the reactor was cooled to room temperature. A deep dark homogeneous solution (19.8 g) was obtained. (1.3 g wt gain based on material charged). A solid material (2.35 g) appeared in the bottom of the product solution after standing overnight. The solid product was analyzed by H-nmr to be: bis-(acetylamino)propyl benzene (A+B) at approx. 21% yield. The liquid product contained two aldehyde products.

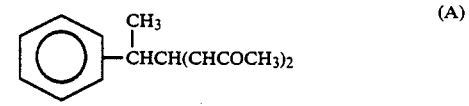

EXAMPLE II

The experimental procedures of Example I were used, except the solvent was ethyl acetate and the molar ratio of CO/H$_2$ was 1:1.

To a glass-lined reactor was charged HRh(CO)(PPh$_3$)$_3$ (0.046 g, 0.050 mmole), dicobalt octacarbonyl (0.34 g, 1.0 mmole) styrene (5.2 g, 0.05 mole), acetamide (3.0 g, 0.05 mole) and ethyl acetate (15.0 g). The reactor was purged of air and pressured to 100 psi with CO/H$_2$ mixture (1:1 molar ratio). The system was heated to 100° C. and the pressure was raised to 2000 psi. After 4 hours reaction time, the reactor was cooled to room temperature. The excess gas was vented. A dark black solution (25.5 g) was recovered with approximately 2.0 g weight gain based on starting material charged. After standing at room temperature the precipitate appeared. The mixture was filtered. A 8.2 g light brown solid was obtained. The H-nmr showed the solid product was Beta-phenyl-N-acetyl-alpha-amino acid. (C) The yield was estimated to be ca. 75% based on styrene charged. The product was further identified by its silyl derivative (D) using BSTFA, (N,O-bis-(trimethylsilyl)-trifluoroacetamide) reagent.

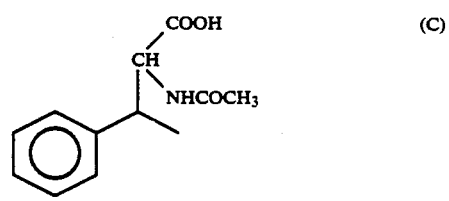

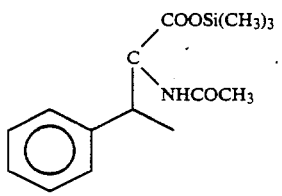

(D)

EXAMPLE III (Comparative Example)

The procedures of Examples I and II were used, except no rhodium catalyst was used.

The reactor was charged with dicobalt octacarbonyl (0.34 g, 1 mmole), styrene (5.2 g, 0.05 mole), acetamide (3.0 g, 0.05 mole) and ethyl acetate (15.0 g). The reaction conditions were 2000 psi pressure where $CO/H_2 = 1:1$ molar ratio, 100° C. and 4 hours. The reaction product contained only ethyl benzene and aldehyde product. There was no N-acetyl amino acid obtained.

This example shows the rhodium catalyst enhances the reaction to achieve the amino acid product. Otherwise, the reduction product ethyl benzene will be formed.

EXAMPLE IV

A 300 ml stirred reactor was charged with $HRh(CO)(PPh_3)_3$ (0.046 g 0.05 mmole), dicobalt octacarbonyl (0.68 g, 2.0 mmole), styrene (5.2 g, 0.05 mole), acetamide (3.0 g, ca. 0.05 mmole) and ethyl acetate (20 g). The reactor was purged of air and pressured to 100 psi. After heating to 100° C., the system was pressured with $CO/H_2$ (1:1 mixture) to 800 psi. During 4 hours reaction time, 140 psi of syngas pressure uptake was recorded. The final product mixture contained 6.0 g solid and 23.3 g liquid. The solid was analyzed by H-nmr, shown to be N-acetyl-beta-phenyl-amino acid.

The yield was estimated to be 55% based on styrene charged.

This example showed the Rh/Co bimetallic catalyst was active even at 800 psi pressure.

EXAMPLE V (Comparative Example)

Identical procedures were used for this example as used in Example IV, except no rhodium catalyst was present.

The reactor was charged with $Co_2(CO)_8$ (0.68 g), styrene (5.2 g), acetamide (3.0 g) and ethyl acetate (20 g). The conditions were 100° C., 800 psi and 4 hours. The recovered liquid product contained no N-acetyl-beta-phenyl-amino acid.

EXAMPLE VI

An experiment was carried out to demonstrate the use of these products as chelating agents in a water solution containing various heavy metals.

First, a solution of nickel, copper and chromium ions was prepared by dissolving nickel (II) nitrate-hydrate, (~1.0 g), copper (II) nitrate-hydrate (1.0 g) and chromium (II) nitrate-hydrate in 300 g de-ionized water. The solution showed 1210 ppm copper (II) 1000 ppm nickel (II) and 470 ppm chromium content by atomic absorption.

Some of the product from Example II (0.50 g) was added to a 15 ml. solution of Ni/Cu/Cr. The two-phase (solid product and metal solution) was shaken vigorously and allowed to stand overnight. The liquid solution was decanted and analyzed. The result showed the nickel concentration dropped from 1000 ppm to 994 ppm, copper from 1210 ppm to 1180 pp and chromium from 470 ppm to 460 ppm, thus demonstrating the ability to extract heavy metals from water. It is believed these procedures could be further optimized.

What is claimed is:

1. A novel phenyl substituted amino acid derivative consisting of a Beta-phenyl-N-acetyl-alpha amino acid represented by the formula:

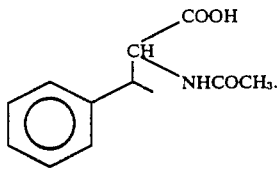

* * * * *